United States Patent [19]

Kitatsuji et al.

[11] Patent Number: 5,514,574
[45] Date of Patent: May 7, 1996

[54] METHOD OF PRODUCING FLAVINE NUCLEOTIDES

[75] Inventors: Katsura Kitatsuji, Tokyo; Shuichi Ishino, Yamaguchi; Sadao Teshiba, Tokyo; Masaru Arimoto, Yamaguchi, all of Japan

[73] Assignee: Kyowa Hakko Kogyo Co., Ltd., Tokyo, Japan

[21] Appl. No.: 279,625

[22] Filed: Jul. 25, 1994

Related U.S. Application Data

[63] Continuation of Ser. No. 973,384, Nov. 10, 1992, abandoned.

[30] Foreign Application Priority Data

Nov. 11, 1991 [JP] Japan ................................. 3-294421

[51] Int. Cl.$^6$ ............................. C12N 9/12; C12N 9/02; C12P 21/06; C12P 19/30
[52] U.S. Cl. ............................. 435/194; 435/69.1; 435/89; 435/172.3; 435/189; 435/252.3; 435/252.32; 435/252.33; 435/252.34; 435/320.1
[58] Field of Search ........................ 435/69.1, 89, 172.3, 435/189, 194, 252.3, 252.32, 252.33, 252.34, 320.1

[56] References Cited

PUBLICATIONS

Derwent Abstract JP 59132898 File 351 004077435 WPI Acc No. 84–222976/36 Acc No. C84–094107 Jul. 31, 1984.
Derwent Abstract JP 2138988 0083199688 WPI Acc No: 90–206689/27 Acc No. C90–0899 May 28, 1990.

Kamio et al J. Biological Chemistry 1986 vol. 260, No. 9, May 10, 1985 pp. 5616–5620 "Characterization of the ileS–lsp Operon . . . ".
Manstein et al J. of Biological Chemistry vol. 261, No. 34 Dec. 5, 1986 pp. 16169–16173 "Purification and Characterization of FAD . . . ".
Glover "Principles of Cloning DHA" *Gene Cloning* pp. 1–20 1984.
Glover "Expression of Cloned DHA . . . " *Gene Cloning* pp. 110–127 1984.
Glover "Reactivation and Mutegavene . . . " Gene Cloning pp. 48–81 1984.
Fujii et al "Activation of Medionine . . . " Arch Biochem Brophys. 178:2 pp. 662–670 (1977).
Glover "Principles of Cloning DNA" *Gene Cloning* pp. 1–20 1984.
Glover "Expression of Cloned DNA" *E. coli* Plasmid *Gene Cloning* pp. 110–127.
Glover "Recombination Imutogenesis . . . " *Gene Cloning* pp. 48–81 1984.

*Primary Examiner*—Robert A. Wax
*Assistant Examiner*—Hyosuk Kim
*Attorney, Agent, or Firm*—Nixon & Vanderhye

[57] ABSTRACT

Flavine nucleotides, which are useful as ingredients of nutrient compositions, raw materials for various pharmaceutical products, biochemical research reagents and so on, are produced from flavine nucleotide precursors and ATP by utilizing cells or a culture of a microorganism which belongs to the genus Escherichia, Enterobactor or Pseudomonas and harbors a recombinant DNA comprising a vector DNA and a DNA fragment carrying the genetic information relevant to the synthesis of FMN and/or FAD, or treated cells or a treated culture of the microorganism.

4 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:1:

CCGGTTAAGC TTGACCGCTG TACAAG        26

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:2:

CCCTGTTTCC GGCGAATTCA GGGTT        25

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:3:

ATCGTATCGA TAAGCTTATG GCCCCGCAAG AAGGGTGTGT GCTGACTATT        50

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:4:

ATCGTATCGA TAAGCTTATG GTGCTGACTA TTGGTAATTT CGACGGCGTG        50

( 2 ) INFORMATION FOR SEQ ID NO:5:

( i ) SEQUENCE CHARACTERISTICS:
        ( A ) LENGTH: 50 base pairs (B) TYPE: nucleic acid
                (C) STRANDEDNESS: single
                (D) TOPOLOGY: linear (ii) MOLECULE TYPE: cDNA (iii) HYPOTHETICAL: N (xi) SEQUENCE DESCRIPTION: SEQ ID NO:5:

ATCGTATCGA TAAGCTTATG GGTCATCGCG CGCTGTTACA GGGCTTGCAG          50

(2) INFORMATION FOR SEQ ID NO:6:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: cDNA (iii) HYPOTHETICAL: N (xi) SEQUENCE DESCRIPTION: SEQ ID NO:6:

GATTTATAGG CATGCATCAG ATTCTCGGAT CCGTATTTCG G                   41

(2) INFORMATION FOR SEQ ID NO:7:

(i) SEQUENCE CHARACTERISTICS:
                (A) LENGTH: 53 base pairs
                (B) TYPE: nucleic acid
                (C) STRANDEDNESS: single
                (D) TOPOLOGY: linear (ii) MOLECULE TYPE: cDNA (iii) HYPOTHETICAL: N (xi) SEQUENCE DESCRIPTION: SEQ ID NO:7:

CGATGAATTC GGATCCGCTC TTATTTCAGT TCGTCCAGCG ACGCAAATCG CTG      53

(2) INFORMATION FOR SEQ ID NO:8:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: cDNA (iii) HYPOTHETICAL: N (xi) SEQUENCE DESCRIPTION: SEQ ID NO:8:

GTGCTGACTA TTCGTAATTT CGACGGCGTC CAT                            33

(2) INFORMATION FOR SEQ ID NO:9:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: cDNA (iii) HYPOTHETICAL: N (xi) SEQUENCE DESCRIPTION: SEQ ID NO:9:

GTGCTGACTA TTGCTAATTT CGACGGCGTC CAT                            33

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:10:

```
GTGCTGACTA TTGATAATTT CGACGGCGTC CAT                              33
```

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( x i ) SEQUENCE DESCRIPTION: SEQ ID NO:11:

```
CCGTTAATCT GCAGGCACTC GTTACG                                     26
```

( 2 ) INFORMATION FOR SEQ ID NO:12:

( i ) SEQUENCE CHARACTERISTICS:
        ( A ) LENGTH: 939 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Escherichia coli ( i x ) FEATURE:
        ( A ) NAME/KEY: CDS
        ( B ) LOCATION: 1..935
        ( D ) OTHER INFORMATION: /product="PROTEIN X"

( x i ) SEQUENCE DESCRIPTION: SEQ ID NO:12:

```
ATG AAG CTG ATA CGC GGC ATA CAT AAT CTC AGC CAG GCC CCG CAA GAA    48
Met Lys Leu Ile Arg Gly Ile His Asn Leu Ser Gln Ala Pro Gln Glu
 1           5                  10                  15

GGG TGT GTG CTG ACT ATT GGT AAT TTC GAC GGC GTG CAT CGC GGT CAT    96
Gly Cys Val Leu Thr Ile Gly Asn Phe Asp Gly Val His Arg Gly His
             20                  25                  30

CGC GCG CTG TTA CAG GGC TTG CAG GAA GAA GGG CGC AAG CGC AAC TTA   144
Arg Ala Leu Leu Gln Gly Leu Gln Glu Glu Gly Arg Lys Arg Asn Leu
         35                  40                  45

CCG GTG ATG GTG ATG CTT TTT GAA CCT CAA CCA CTG GAA CTG TTT GCT   192
Pro Val Met Val Met Leu Phe Glu Pro Gln Pro Leu Glu Leu Phe Ala
     50                  55                  60

ACC GAT AAA GCC CCG GCA AGA CTG ACC CGG CTG CGG GAA AAA CTG CGT   240
Thr Asp Lys Ala Pro Ala Arg Leu Thr Arg Leu Arg Glu Lys Leu Arg
 65                  70                  75                  80

TAC CTT GCA GAG TGT GGC GTT GAT TAC GTG CTG TGC GTG CGT TTC GAC   288
Tyr Leu Ala Glu Cys Gly Val Asp Tyr Val Leu Cys Val Arg Phe Asp
             85                  90                  95

AGG CGT TTC GCG GCG TTA ACC GCG CAA AAT TTC GTC AGC GAT CTT CTG   336
Arg Arg Phe Ala Ala Leu Thr Ala Gln Asn Phe Val Ser Asp Leu Leu
        100                 105                 110

GTG AAG CAT TTG CGC GTA AAA TTT CTT GCC GTA GGT GAT GAT TTC CCT   384
```

|     |     |     |     |     |     |     |     |     |     |     |     |     |     |     |     |
|-----|-----|-----|-----|-----|-----|-----|-----|-----|-----|-----|-----|-----|-----|-----|-----|
| Val | Lys | His | Leu | Arg | Val | Lys | Phe | Leu | Ala | Val | Gly | Asp | Asp | Phe | Pro |
|     | 115 |     |     |     | 120 |     |     |     |     |     | 125 |     |     |     |     |

```
TTG GCG CTG GTC GTG AAG GCG ATT TCT TGT TAT TAC AGA AAG CTG GCA     432
Leu Ala Leu Val Val Lys Ala Ile Ser Cys Tyr Tyr Arg Lys Leu Ala
    130             135             140

TGG AAT ACG GCT TCG ATA TCA CCA GTA CGC AAA CTT TTT GCA GAG GTG     480
Trp Asn Thr Ala Ser Ile Ser Pro Val Arg Lys Leu Phe Ala Glu Val
145             150             155                             160

GCG TGC GCA TCA GCA GCA CGG CTG CGT CAG GCC CTT GCG GAT GAC AAT     528
Ala Cys Ala Ser Ala Ala Arg Leu Arg Gln Ala Leu Ala Asp Asp Asn
            165             170                 175

CTG GCT CTG GCA GAG AGT TTA CTG GGG CAC CCG TTT GCC ATC TCC GGG     576
Leu Ala Leu Ala Glu Ser Leu Leu Gly His Pro Phe Ala Ile Ser Gly
            180             185                 190

CGT GTA GTC CAC GGT GAT GAA TTA GGG CGC ACT ATA GGT TTC CCG ACG     624
Arg Val Val His Gly Asp Glu Leu Gly Arg Thr Ile Gly Phe Pro Thr
        195             200             205

GCG AAT GTA CCG CCG CGC CGT CAG GTT TCC CCG GTC AAA GGG GTT TAT     672
Ala Asn Val Pro Pro Arg Arg Gln Val Ser Pro Val Lys Gly Val Tyr
    210             215             220

GCG GTA GAA GTG CTG GGC CTC GGT GAA AAG CCG TTA CCC GGC GTG GCA     720
Ala Val Glu Val Leu Gly Leu Gly Glu Lys Pro Leu Pro Gly Val Ala
225             230             235                             240

AAC ATC GGA ACA CGC CCA ACG GTT GCC GGT ATT CGC CAG CAG CTG GAA     768
Asn Ile Gly Thr Arg Pro Thr Val Ala Gly Ile Arg Gln Gln Leu Glu
            245             250             255

GTG CAT TTG TTA GAT GTT GCA ATG GAC CTT TAC GGT CGC CAT ATA CAA     816
Val His Leu Leu Asp Val Ala Met Asp Leu Tyr Gly Arg His Ile Gln
        260             265             270

GTA GTG CTG CGT AAA AAA ATA CGC AAT GAG CAG CGA TTT GCG TCG CTG     864
Val Val Leu Arg Lys Lys Ile Arg Asn Glu Gln Arg Phe Ala Ser Leu
        275             280             285

GAC GAA CTG AAA GCG CAG ATT GCG CGT GAT GAA TTA ACC GCC CGC GAA     912
Asp Glu Leu Lys Ala Gln Ile Ala Arg Asp Glu Leu Thr Ala Arg Glu
    290             295             300

TTT TTT GGG CTA ACA AAA CCG GCT TAA                                 939
Phe Phe Gly Leu Thr Lys Pro Ala
305             310
```

METHOD OF PRODUCING FLAVINE NUCLEOTIDES

This is a continuation of application Ser. No. 07/973,384, filed Nov. 10, 1992, now abandoned.

FIELD OF THE INVENTION

The present invention relates to a process for producing flavine nucleotides, in particular flavine mononucleotide (FMN) and/or flavine adenine dinucleotide (FAD), using microorganisms.

FMN and FAD, which are coenzyme forms of vitamin $B_2$, are not only useful as raw materials for preparing nutrient compositions or producing various drugs but also important as reagents to be used in biochemistry. They are used in various fields of bioindustry.

BACKGROUND OF THE INVENTION

Various methods are known for the production of flavine nucleotides. Thus, mention may be made of, for instance, the method disclosed in JP-A-132898/84 which uses a microorganism belonging to the genus Corynebacterium or Brevibacterium and capable of forming adenosine-5'-triphosphate (ATP) from an ATP precursor, a phosphate donor and an energy donor and further capable of forming FAD from FMN and ATP, and the method disclosed in JP-A-138988/90 which uses a microorganism belonging to the genus Corynebacterium or Brevibacterium and harboring a recombinant DNA which contains a DNA fragment carrying the genetic information relevant to the synthesis of FMN or FAD as derived from a microorganism belonging to the genus Corynebacterium or Brevibacterium (the term "JP-A" used herein means an unexamined published Japanese patent application).

Further it is known that, in microorganisms belonging to the genus Brevibacterium, the flavokinase (FK) activity for the formation of FMN from riboflavine (FR) and ATP and the flavine adenine dinucleotide synthetase (FADS) activity for the formation of FAD from FMN and ATP occur on one and the same protein [Journal of Biological Chemistry, 261, 16169–16173 (1986)].

However, no methods are known for using microorganisms belonging to the genus Escherichia, Enterobacter or Pseudomonas and harboring a recombinant DNA which contains a DNA fragment carrying the genetic information relevant to the synthesis of FMN and/or FAD.

SUMMARY OF THE INVENTION

An object of the invention is to produce flavine nucleotides, which are important as ingredients of nutrient compositions, raw materials for preparing various drugs and reagents for biochemical research, among others, in high yields and in an inexpensive manner.

The present invention provides a process for producing flavine nucleotides which comprises reacting a flavine nucleotide precursor with ATP in an aqueous medium in the presence of cells or a culture of a microorganism harboring a recombinant DNA which contains a DNA fragment derived from a microorganism belonging to the genus Escherichia, Enterobactor or Pseudomonas and carrying the genetic information relevant to the synthesis of FMN and/or FAD, or treated cells or a treated culture of the microorganism, until a recoverable amount of the flavine nucleotide is accumulated in the aqueous medium and recovering the thus-formed flavine nucleotide from the aqueous medium.

DETAILED DESCRIPTION OF THE INVENTION

Usable as a flavine nucleotide precursor are riboflavine and flavine mononucleotide. Flavine nucleotides to be produced include flavine nononucleotide and flavine adenine dinucleotide.

As said DNA fragment, there may be mentioned a DNA fragment containing the whole or a part of the gene coding for a protein having the FK activity and FADS activity or a DNA fragment containing the whole or a part of the gene coding for a modified protein of the above-mentioned protein, which retains the FK activity but has no or reduced FADS activity. The DNA sequence of the gene coding for protein X and the deduced amino acid sequence are shown in SEQ ID No:12. An example of the former is a DNA fragment containing the whole or a part of the gene coding for protein X [Journal of Biological Chemistry, 260, 5616–5620 (1985)]. An example of the latter is a DNA fragment containing the whole or a part of the gene coding for an amino acid sequence of protein X in which the 23rd glycine residue is substituted with an amino acid other than glycine. As the substituent amino acid, arginine, alanine, aspartic acid and the like are appropriate.

The microorganism to serve as a source of the DNA fragment may be any of microorganisms belonging to the genus Escherichia, Enterobacter, Pseudomonas or the like provided that it has both the FK activity and FADS activity, it has the FK activity and has no or reduced FADS activity or it contains the whole or a part of the gene coding for protein X. Specific examples of the microorganism having both the FK and FADS activities include *Escherichia coli* K12 and a mutant thereof, *Escherichia coli* C600 [Appleyard, R. K., Genetics, 39, 440 (1954)]. While it was unknown whether the FK activity and FADS activity in microorganisms belonging to the genus Escherichia occur on one and the same protein or on different proteins, isolation and subsequent analysis of the relevant genes from a microorganism belonging to the genus Escherichia by the present inventors has revealed that, as in microorganisms belonging to the genus Brevibacterium, both the activities occur on one and the same protein (protein X) and there are a domain for the FADS activity in the N terminal portion and a domain for the FK activity at the C terminal portion. This indicates that, like microorganisms belonging to the genus Brevibacterium, microorganisms belonging to the genus Escherichia have an activity for the formation of FAD from FR and ATP via FMN. The use of such microorganisms makes it possible to use not only FR but also FMN as the substrate, and is effective in the production of FMN and FAD from FR and in the production of FAD from FMN as well. It is to be noted however, that the genes to be used in accordance with the present invention are clearly different from the genes derived from microorganisms belonging to the genus Brevibacterium, since *Escherichia coli* strains have no genes hybridizable with the genes derived from microorganisms belonging to the genus Brevibacterium.

A gene coding for a modified protein X which retains the FK activity but has no or reduced FADS activity can be prepared by replacing the 23rd amino acid residue glycine from the N terminal of protein X with an amino acid other than glycine by means of site-directed mutagenesis using Mutant-K kit (Takara Shuzo). This modified protein is useful for production of FMN alone without coproduction of FAD.

The host microorganism to be used in the practice of the invention may be any of wild strains, drug-resistant and/or auxotrophic mutants and other strains belonging to the genus Escherichia, Enterobacter or Pseudomonas provided that the microorganism is capable of incorporating DNA. A preferred example is *Escherichia coli* DH5α [Bethesda Research Laboratories, Focus, 8, 9 (1986)].

The vector to be used in the practice of the invention may be a phage vector, a plasmid vector or the like provided that it is capable of autonomous replication in strains of the genus Escherichia, Enterobacter or Pseudomonas. Preferred examples are pBR322 [Gene, 2, 95 (1977)] and pUC19 [Gene, 33, 103 (1985)]. Host-vector systems of other microorganisms, for example, of the genus Brevibacterium or Corynebacterium, may also be used.

A recombinant DNA Can be obtained from the above-described DNA fragment carrying the genetic information relevant to the synthesis of FMN and/or FAD and the vector DNA, together with various recombinant hybrids, by cleaving both DNAs in vitro with a restriction enzyme or enzymes to give fitting cleavage ends and then carrying out the ligation reaction using a DNA ligase.

The thus-obtained recombinant hybrid mixture or ligation mixture is used to transform a host microorganism selected from among microorganisms belonging to the genus Escherichia, Enterobacter or Pseudomonas, and a transformant harboring the recombinant plasmid containing the DNA fragment carrying the genetic information relevant to the synthesis of FMN and/or FAD is selected. The recombinant plasmid containing said DNA can be obtained by plasmid isolation from said strain.

The transformation can be carried out by the method of Cohen et al. [Proc. Natl. Acad. Sci. USA, 69, 2110 (1972)].

For selecting a transformant harboring the recombinant plasmid containing the DNA fragment carrying the genetic information relevant to the synthesis of FMN and/or FAD when the whole or a part of the amino acid sequence corresponding to said DNA is known, use is made of, for instance, the selection method comprising synthesizing a DNA oligomer having a base sequence corresponding to said amino acid sequence and utilizing, as a probe, the ability to hybridize with this DNA.

Then, said DNA fragment is excised from the recombinant plasmid obtained as described above by means of an appropriate restriction enzyme or enzymes. This DNA fragment is inserted into a vector DNA capable of autonomous replication in the host microorganism to give a recombinant plasmid containing said DNA. The recombinant plasmid is used to transform the host microorganism by the method of Cohen et al. to give a desired transformant.

The thus-obtained transformant (a strain with high level expression of FK-FADS or FK) can be cultivated by a conventional method of bacterial cultivation in an ordinary synthetic or natural medium containing carbon source(s), nitrogen source(s), inorganic substance(s), amino acid(s), vitamin(s) and so forth under aerobic conditions while the temperature and pH and other conditions are suitably adjusted. The high-density cultivation method [Biotechnology and bioengineering, 17, 227–239 (1975)] is particularly preferred.

The carbon sources to be used in the medium include carbohydrates, such as glucose, fructose, sucrose, molasses, waste molasses and starch hydrolyzates, alcohols, such as ethanol, glycerol and sorbitol, organic acids, such as pyruvic acid, lactic acid and acetic acid, amino acids, such as glycine, alanine, glutamic acid and aspartic acid, and other organic materials assimilable by said microorganism. These are used desirably in a concentration of 0.5 to 30%.

Usable as the nitrogen sources are ammonia, various inorganic and organic ammonium salts, such as ammonium chloride, ammonium sulfate, ammonium nitrate, ammonium carbonate, ammonium acetate and ammonium phosphate, nitrogen-containing organic compounds, such as urea, peptone, NZ amine, meat extract, yeast extract, corn steep liquor, casein hydrolyzates, fish meal and digestion products derived therefrom, various amino acids, such as glycine and glutamic acid, and so forth. They are used suitably in a concentration of 0.1 to 10%.

Usable as the inorganic substances are, for instance, potassium dihydrogenphosphate, dipotassium hydrogenphosphate, magnesium sulfate, magnesium phosphate, sodium chloride, ferrous sulfate, manganese sulfate, zinc sulfate and calcium carbonate. Where the microorganism used requires a specific nutrient, for example an amino acid, a nucleic acid or a vitamin, for its growth, an appropriate amount of such nutrient substance should be added to the medium.

The cultivation is carried out under aerobic conditions, for example with shaking or with aeration and agitation. A cultivation temperature of 28° to 42° C. is generally best suited. The cultivation will be complete in 1 to 24 hours. Generally, pH of the medium should desirably be maintained within a substantially neutral range using ammonia, urea, aqueous sodium hydroxide or the like.

While the thus-obtained culture of the transformant may be used as such in the subsequent reaction step, it is possible to use treated cells or treated culture of the transformant in any of various ways. Such treated cells or a treated culture includes, among others, culture broth concentrates, dried culture broth, surfactant-treated culture broth, bacteriolytic enzyme-treated culture broth, cells obtained by centrifugation of the culture, dried cells, acetone-treated cells, surfactant-treated cells, bacteriolytic enzyme-treated cells and immobilized cells.

The reaction can be carried out in any aqueous medium. Preferably, FR or FMN and ATP, if necessary together with a surfactant and/or an organic solvent, are added simultaneously in the microbial culture broth or, after completion of the cultivation, FR or FMN and ATP, if necessary together with a surfactant and/or an organic solvent, are added to the culture or culture cells or treated cells or a treated culture and the reaction is carried out at 20° to 50° C. for 1 to 72 hours, whereby a flavine nucleotide is accumulated in the culture broth or reaction mixture. On that occasion, the pH should desirably be adjusted to 6 to 9 and the oxidation reduction potential to −250 to −400 mV. The substrate concentrations in the culture medium or reaction mixture are generally as follows: FR 0.1 to 20 g/liter, FMN 0.1 to 40 g/liter and ATP 0.1 to 100 g/liter. In the case of using the cells (transformants) or treated cells which can exert high FK and/or FADS activities, the cell concentration in the culture medium or reaction mixture is preferably adjusted to 5 to 200 g/liter (wet cells). Although FR is sparingly soluble in water, the desired object can be acheived in a state in which FR is undissolved but suspended in water.

As for the ATP source, not only highly purified preparations but also ATP-containing solutions obtained by contacting adenine with microbial cells in the presence of an energy donor (cf. JP-A-51799/81), filtrates derived therefrom by removing cells or concentrates thereof can be used. It is also possible to synthesize and supply ATP from glucose and inorganic phosphate by adding a microorganism having ATP-regenerating activity (cf. JP-A-74595/86) to the reaction system. In this case, the reaction is carried out in the presence of an ATP precursor, an ATP-regenerating energy donor, a phosphate group donor and a microorganism having ATP biosynthesizing activity occurred in the reaction mixture in lieu of ATP. As the microbial strain having ATP-regenerating activity to be used in this case, there may be mentioned, for example *Brevibacterium ammoniagenes* [currently *Corynebacterium ammoniagenes*, cf, International Journal of Systematic Bacteriology, 34 (4), 442 (1987); hereinafter referred to as *Corynebacterium ammoniagenes*] ATCC 21170 and *Escherichia coli* ATCC 11303. The cultivation for obtaining microbial cells having ATP-regenerating activity is carried out by the method described in JP-A-74595/86.

As said surfactant, there may be mentioned, for instance, cationic surfactants, such as polyoxyethylene-stearylamine (e.g. Nymine S-215, product of Nippon Oil & Fats Co.), cetyltrimethylammonium bromide and cetylpyridinium chloride, anionic surfactants, such as sodium lauryl sulfate and sodium oleylamidosulfate, nonionic surfactants, such as polyoxyethylenesorbitan monostearate (e.g. Nonion ST221, product of Nippon Oil & Fats Co.), and amphoteric surfactants, such as laurylbetaine (e.g. Anon BF, product of Nippon Oil & Fats Co.). These are used generally in a concentration of 0.1 to 50 g/liter, preferably 1 to 20 g/liter.

The organic solvent is, for example, toluene, xylene, acetone, an aliphatic alcohol or ethyl acetate. It is used generally in an amount of 0.1 to 50 ml/liter, preferably 1 to 20 ml/liter.

The flavine nucleotide accumulated in the medium or reaction mixture can be recovered by a conventional method using activated carbon, an ion exchange resin, or the like.

The following examples are further illustrative of the invention, but are not to be construed to limit the scope of the invention.

EXAMPLE 1

Preparation of a Microorganism Capable of High Expression of FK-FADS and a Microorganism Capable of High Expression of FK (1) Purification of FK-FADS An *Escherichia coli* C600 culture broth was subjected to centrifugation to give 30 g of wet cells. These were suspended in 100 ml of purification buffer (I) [50 mM Tris-hydrochloride (pH 8), 0.1 mM ethylenediaminetetraacetic acid (EDTA), 1 mM dithiothreitol] and disrupted using a homogenizer (product of Brown Biotech; glass bead diameter 0.1 mm). The disruption mixture was centrifuged to give about 90 ml of a supernatant. Protamine sulfate was added to the supernatant to a final concentration of 0.4%, and the resulting mixture was centrifuged for removing macromolecular nucleic acid components as a sediment. The supernatant obtained was dialyzed against purification buffer (I) through a cellulose membrane to give a desalted active fraction (about 11 ml). This fraction was applied to a CM-Sepharose column (Pharmacia) previously equilibrated with purification buffer (I) and the desired enzyme was eluted with 300 ml of purification buffer (I) with a linear NaCl concentration gradient of 0M to 1M. From among the active fractions obtained, a 12-ml portion maximal in enzyme activity was taken. This active fraction was applied to a Sephacryl S-300 column (Pharmacia), and elution was carried out with purification buffer (I). This gel filtration gave 5 ml of an active fraction. This fraction was applied to an ATP-agarose column previously equilibrated with purification buffer (I). Elution was carried out using 100 ml of purification buffer (I) with a linear NaCl concentration gradient of 0M to 1M and active fractions were collected. Finally, there was obtained 3.5 ml of a purified enzyme fraction with a protein content of 16.7 μg/ml.

(2) Isolation of an FK-FADS gene

The purified enzyme obtained as described above was subjected to SDS-polyacrylamide electrophoresis, followed by blotting onto a PVDF (polyvinylidene difluoride) membrane and N-terminal amino acid sequence determination. Fourteen N-terminal amino acids were found identical with those of protein X. Therefore, based on the protein X nucleotide sequence [Kamio, Y. et al., Journal of Biological Chemistry, 260, 5616–5620 (1985)], a 5'-end primer (SEQ ID NO: 1) and a 3'-end primer (SEQ ID NO: 2) were designed for PCR (polymerase chain reaction). These were synthesized by the phosphoamidite method for solid phase synthesis [Beaucage, S. L. et al., Tetrahedron Letters, 22, 1859 (1985)] using an Applied Biosystems model 380A automated DNA synthesizer. The PCR was carried out using a GeneAmp DNA amplification reagent kit (Takara Shuzo). The chromosomal DNA of *Escherichia coli* C600 was used as the template in an amount of 1 ng/100 μl, the synthetic DNA primers were used each in a concentration of 1.0 μM, dATP, dCTP, dGTP and dTTP were used each in a concentration of 200 μM and Taq DNA polymerase (Takara Shuzo) was used in an amount of 2.5 units/100 μl. Each reaction cycle consisted of 92° C.×1 minute, 37° C.×2 minutes and 70° C.×3 minutes. After 25 cycles, the desired DNA fragment coding for protein X was obtained.

(3) Preparation of a recombinant DNA

To 20 μl of a solution containing 1 μg of the DNA fragment obtained as described above were added HindIII and EcoRI, and digestion was carried out. Separately, HindIII and EcoRI were added to 20 μl of a solution containing 1 μg of the vector pUC19 and digestion was carried out. The thus-digested DNA fragment and vector DNA were purified by phenol extraction and ethanol precipitation. The purified DNA (100 ng) and the purified vector DNA (20 ng) were suspended in a solution containing 66 mM Tris-hydrochloride buffer (pH 7.6), 66 mM magnesium chloride, 10 mM DTT and 0.1 mM ATP, 10 units of T4 ligase was added, and the ligation reaction for joining both DNAs to each other was carried out at 14° C. for 16 hours to give a recombinant DNA.

(4) Preparation of an *Escherichia coli* strain harboring the recombinant DNA

*Escherichia coli* DH5α was inoculated into 50 ml of LB liquid medium [1% Bacto-tryptone, 0.5% Bacto-yeast extract, 1% sodium chloride (pH 7.5)] and cultured at 37° C. for 4 hours. Cells were collected by centrifugation at 3,000 revolutions per minute (rpm) for 7 minutes and suspended in 20 ml of 50 mM calcium chloride solution maintained at 0° C. After standing at 0° C. for 20 minutes, the cells were collected by the same centrifugation procedure as mentioned above and suspended in 40 ml of 50 mM calcium chloride solution maintained at 0° C. This suspension was mixed with the recombinant DNA-containing solution obtained as described in (3) of Example 1, and the mixture was allowed to stand at 0° C. for 10 minutes, then heat-treated at 42° C. for 90 seconds and spread over an LB agar plate medium (LB liquid medium+1.5% agar) containing 50 μg/ml of ampicillin and 20 μg/ml of 5-bromo-4-chloro-3-indolyl-β-galactoside (Xgal). This plate medium was incubated at 37° C. for 24 to 48 hours.

(5) Isolation of a DNA coding for FK-FADS

After the above incubation, colonies appeared on the plate medium. Among the colonies, white colonies were cultured each individually in LB liquid medium. For each colony, wet cells of a transformant were obtained. The cells obtained were disrupted by the method described in (1) of Example 1 and a supernatant was collected. This supernatant was regarded as a crude enzyme and subjected to the assay of activity by the method of D. J. Manstein et al. [Journal of Biological Chemistry, 261, 16169–16173 (1986)] using FR or FMN as the substrate. As a result, a strain about 325 times stronger in FK activity and about 240 times stronger in FADS activity was found, as shown in Table 1. The recombinant plasmid harbored in said strain was named pFK5A and this strain was designated as *Escherichia coli* DH5α/pFK5A.

Said strain has been deposited since Nov. 7, 1991 with the Fermentation Research Institute, Agency of Industrial Science and Technology under the Budapest Treaty. The accession number is FERM BP-3643.

(6) Confirmation of the position of FK and FADS domains

Recombinant plasmids carrying the FK-FADS gene in which the region encoding the N terminal region was deleted were constructed for confirming the position of FK and FADS domains in the FK-FADS encoding gene obtained in the above (5).

The PCR was carried out using a 5'-end primer (SEQ ID NO: 3, 4 and 5), a 3'-end primer (SEQ ID NO: 6) and pFK5A as a template in the same manner as described in Example 1-(2) and (3). The thus-obtained HindIII-BamHI fragments were each inserted into an ATG expression vector pTrS33 (JP-A-227075/90) to give recombinant plasmids pND12, pND18 and pND30. These recombinant plasmids contain the FK-FADS gene which lacked the region coding for 12, 18 or 30 amino acid residues from the N terminal. Separately, the HindIII-BamHI fragment, which was a PCR product prepared by using a 5'-end primer (SEQ ID NO: 1), a 3'-end primer (SEQ ID NO: 7) and pFK5A as a template in the same manner as described in Example 1-(2) and (3), was inserted into pUC19 to obtain a recombinant plasmid pCD20. This plasmid contains the FK-FADS gene which lacked the region coding for 20 amino acid residues from the C terminal.

The recombinant plasmids thus obtained were each used to transform *Escherichia coli* DH5α. The crude extract were prepared from the transformants and assayed for enzyme activities in the same manner as described in Example 1-(5). The results are shown in Table 1.

The results suggest that an FADS domain exists in the N terminal region of protein X (FK-FADS) since the FADS activity is remarkably reduced when at least 18 amino acid residues from the N terminal are deleted and that an FK domain exists in the C terminal region of the protein. The crude extract obtained from the culture supernatant of the deletion mutant-containing cells showed lower activity than that of the pFK5A-containing cells. It is considered that the decrease in activity was caused by formation of inclusion bodies during cultivation, which decreased soluble enzymes.

TABLE I

| Strain | FK activity (Unit/mg protein) | FADS activity (Unit/mg protein) |
| --- | --- | --- |
| DH5α | 0.08 (1)* | 0.15 (1) |
| DH5α/pFK5A | 27.6 (329) | 37.6 (245) |
| DH5α/pND12 | 6.96 (83) | 8.13 (53) |
| DH5α/pND18 | 3.61 (43) | 0.31 (2) |
| DH5α/pND30 | 4.53 (54) | 0.31 (2) |
| DH5α/pCD20 | 0.17 (2) | 1.07 (7) |

TABLE I-continued

| Strain | FK activity (Unit/mg protein) | FADS activity (Unit/mg protein) |
| --- | --- | --- |

*Parenthetic values are a ratio of the activity to that obtained from non-transformed cells of *E. coli* DH5α.

(7) Preparation of a microorganism having reduced FADS activity

Using primers each specified in SEQ ID NO: 8, 9 and 10, respective recombinant plasmids were prepared according to the Kunkel method [Methods in Enzymology, 154, 364 (1987)]. The primers specified in SEQ ID No:8, 9 and 10 were designed so that the 23rd glycine of protein X should be replaced with arginine, alanine and aspartic acid, respectively. The PstI-EcoRI fragment obtained through RCR using primers specified in SEQ ID NO:2 and 11 was inserted into plasmid pTZ19R [Protein Engineering, 1, 67 (1986)] to obtain a plasmid harboring the wild FK-FADS gene to be used as a template. Mutation was confirmed by analyzing the recombinant plasmid isolated from the transformant with an automatic DNA sequencer. Plasmids on which the mutation was conferred for substitution of the 23rd glycine codon of protein X with the arginine codon, alanine codon or aspartic acid codon were named plasmids pKK11, pKK12 and pKK13, respectively. Each mutated plasmid was used to transform *Escherichia coli* DH5α to give transformants, DH5α/pKK11, DH5α/pKK12 and DH5α/pKK13. The enzyme activity was measured using the crude extract of these strains in the same manner as in Example 1-(5). The results are shown in Table 2. From the results, it can be seen that protein X mutein in which the 23rd glycine was replaced with arginine alanine or aspartic acid retained the FK activity but almost lost the FADS activity. *Escherichia coli* DH5α/pKK11, DH5α/pKK12 and DH5α/pKK13 have been deposited since Oct. 13, 1992 with the Fermentation Research Institute, Agency of Industrial Science and Technology under the accession Nos. FERM BP-4031, FERM BP-4032 and FERM BP-4033, respectively, in accordance with the Budapest Treaty.

TABLE 2

| Strain | FK activity (Unit/mg protein) | FADS activity (Unit/mg protein) |
| --- | --- | --- |
| DH5α | 0.09 (1)* | 0.15 (1) |
| DH5α/pFK5A | 28.5 (325) | 36.2 (240) |
| DH5α/pKK11 | 17.3 (200) | 1.18 (8) |
| DH5α/pKK12 | 18.2 (210) | 0.74 (5) |
| DH5α/pKK13 | 21.9 (253) | 0.89 (6) |

*Parenthetic values are a ratio of the activity to that obtained from non-transformed cells of *E. coli* DH5α.

EXAMPLE 2

A reaction mixture containing 100 g/liter of cells of *Escherichia coli* DH5α/pFK5A as cultured by the high-density cultivation method, 10 g/liter of FR, 15 g/liter of ATP, 10 ml/liter of xylene and 4 g/liter of Nymine S-215 was poured into a large-size test tube (21 mm in inner diameter), and incubated at 46° C. for 30 hours with occasional shaking to inhibit sedimentation of cells while the pH was adjusted to 7.0 to 7.2 with 0.2N potassium hydroxide. The amounts of $FMN.Na_2$ and $FAD.Na_2$ thus formed are shown in Table 3. The results obtained by using *Escherichia coli* DH5α, DH5α/pKK11, DH5α/pKK12 and DH5α/pKK13 in lieu of Escherichia coli DH5α/pFK5A in the same procedure as described above are also shown in Table 3.

TABLE 3

| Strain | FMN.Na$_2$ (g/liter) | FAD.Na$_2$ (g/liter) |
| --- | --- | --- |
| DH5α | 0.04 | 0.1 |
| DH5α/pFK5A | 1.6 | 3.4 |
| DH5α/pKK11 | 1.4 | 0.1 |
| DH5α/pKK12 | 1.5 | 0.1 |
| DH5α/pKK13 | 1.3 | 0.1 |

EXAMPLE 3

A 10-ml portion of a reaction mixture containing 100 g/liter of cultured cells of *Escherichia coli* DH5α/pFK5A as cultured by the high-density cultivation method, 20 g/liter of FMN, 25 g/liter of ATP, 10 ml liter of xylene and 4 g/liter of Nymine S-215 was poured in a large-size test tube and incubated at 46° C. for 24 hours with occasional shaking to inhibit sedimentation of cells, the pH being adjusted to 7.0 to 7.2 with 0.2N potassium hydroxide. The amount of FAD.Na$_2$ thus formed is shown in Table 4. The same procedure was carried out using *Escherichia coli* DH5α in lieu of *Escherichia coli* DH5α/pFK5A. Further, using 200 g/liter of ATCC 21170/pKH43 (JP-A-138988/90) which is a *Corynebacterium ammoniagenes* strain carrying a plasmid having the FK-FADS gene derived from *Corynebacterium ammoniagenes*, the same procedure was carried out except that the FMN concentration was 12 g/liter, the ATP concentration was 24 g/liter, the reaction temperature was 37° C. and the reaction period was 20 hours. These results are also shown in Table 4.

TABLE 4

| Strain | FAD.Na$_2$(g/liter) |
| --- | --- |
| DH5α | 0.3 |
| DH5α/pFK5A | 18.5 |
| ATCC 21170/pKH43 | 10.7 |

EXAMPLE 4

A 10-ml portion of a reaction mixture containing 100 g/liter of cultured cells of *Escherichia coli* DH5α/pFK5A as cultured by the high-density cultivation method, 1 g/liter of FR, 10 ml/liter of xylene and 4 g/liter of Nymine S-215 was poured in a large-size test tube and incubated at 46° C. for 48 hours with occasional shaking to inhibit sedimentation of cells, the pH being adjusted to 7.0 to 7.2 with 0.2N potassium hydroxide. The amounts of FMN.Na$_2$ and FAD.Na$_2$ thus formed are shown in Table 5. The results obtained by using *Escherichia coli* DH5α, DH5α/pKK11, DH5α/pKK12 and DH5α/pKK13 in lieu of *Escherichia coli* DH5α/pFK5A in the same procedure as described above are also shown in Table 5.

TABLE 5

| Strain | FMN.Na$_2$(g/liter) | FAD.Na$_2$(g/liter) |
| --- | --- | --- |
| DH5α | 0.01 | 0 |
| DH5α/pFK5A | 0.53 | 0.33 |

TABLE 5-continued

| Strain | FMN.Na$_2$(g/liter) | FAD.Na$_2$(g/liter) |
| --- | --- | --- |
| DH5α/pKK11 | 0.41 | 0 |
| DH5α/pKK12 | 0.60 | 0 |
| DH5α/pKK13 | 0.51 | 0 |

EXAMPLE 5

A 500-ml portion of a reaction mixture containing 20 g/liter of cultured cells of *Escherichia coli* DH5α/pFK5A as cultured by the high-density cultivation method, 160 g/liter of cultured cells of *Corynebacterium ammoniagenes* ATCC 21170 as cultured by the method described in JP-A-Sho-61-74595, 100 g/liter of glucose, 16 g/liter of FR, 20 g/liter of KH$_2$PO$_4$, 3 g/liter of NgCl$_2$.7H$_2$O, 10 ml/liter of xylene and 4 g/liter of Nymine S-215 was poured into a 2-liter small-size fermentor and incubated at 46° C. for 48 hours with agitation at 600 rpm while the oxidation reduction potential was maintained at −350 to −400 mV and the pH was adjusted to 7.0 with 5N potassium hydroxide. The amounts of FMN.Na$_2$ and FAD.Na$_2$ thus formed are shown in Table 6. The results obtained by using *Escherichia coli* DH5α and DH5α/pKK12 in lieu of *Escherichia coli* DH5α/pFK5A in the same procedure as described above are also shown in Table 6.

Further, using ATCC 21170/pKH43 (JP-A-2-138988) which is a *Corynebacterium ammoniagenes* stain carrying a plasmid having the FK-FADS gene derived from *Corynebacterium ammoniagenes* and the same procedure was repeated except that the reaction was carried out by pouring a 500-ml portion of a reaction mixture containing 160 g/liter of cultured cells, 100 g/liter of glucose, 8 g/liter of FR, 20 g/liter of KH$_2$PO$_4$, 5 g/liter of MgSO$_4$.7H$_2$O, 10 g/liter of ZnSO$_4$, 40 g/liter of sodium pyrophosphate, 10 g/liter of xylene and 4 g/liter of Nymine S-215 into a 2-liter small-size fermentor and incubating the reaction mixture at 38° C. for 55 hours with agitation at 600 rpm while maintaining the oxidation reduction potential of −300 to −400 mV, the pH of 7.8 with 5N potassium hydroxide and the soluble KH$_2$PO$_4$ concentration of about 30 g/liter with optionally adding KH$_2$PO$_4$. The results are also shown in Table 6.

TABLE 6

| Strain | FMN.Na$_2$(g/liter) | FAD.Na$_2$(g/liter) |
| --- | --- | --- |
| DH5α | 0.1 | 0 |
| DH5α/pFK5A | 15.1 | 1.2 |
| DH5α/pKK12 | 10.1 | 0.05 |
| ATCC 21170/pKH43 | 5.1 | 1 |

In accordance with the present invention, flavine nucleotides, which are important as ingredients of nutrient compositions, raw materials for various pharmaceuticals, biochemical research reagents and so forth, can be produced in high yields and at low cost.

While the invention has been described in detail and with reference to specific embodiments thereof, it will be apparent to one skilled in the art that various changes and modifications can be made therein without departing from the spirit and scope of the invention.

What is claimed is:

1. A process for producing flavin mononucleotide, flavin adenine dinucleotide or both which comprises the steps of:

(1) reacting a riboflavin and/or flavin mononucleotide with adenosine-5'-triphosphate in an aqueous medium in the presence of cells of a microorganism belonging to the genus Escherichia which harbors a recombinant DNA containing a DNA fragment which contains a gene coding for protein X, which is derived from *Escherichia coli*, has flavokinase activity and flavin adenine dinucleotide synthetase activity and has an amino acid sequence illustrated by SEQ ID No:12, or a culture of the microorganism, or treated cells of the microorganism, or a treated culture of the microorganism, until a recoverable amount of flavin mononucleotide and/or flavin adenine dinucleotide is accumulated in the aqueous medium; and (2) recovering the flavin mononucleotide and/or flavin adenine dinucleotide thus formed from the aqueous medium.

2. A process for producing flavin mononucleotide which comprises the steps of:

(1) reacting a riboflavin with adenosine-5'-triphosphate in an aqueous medium in the presence of cells of a microorganism belonging to the genus Escherichia which harbors a recombinant DNA containing a DNA fragment which contains a gene coding for the amino acid sequence of a modified protein X which has flavokinase activity and the amino acid sequence of protein X derived from *Escherichia coli* and has an amino acid sequence illustrated by SEQ ID NO:12 except that glycine at the residue number 23 is substituted with an amino acid selected from the group consisting of alanine, arginine and aspartic acid, or a culture of the microorganism, or treated cells of the microorganism, or a treated culture of the microorganism, until a recoverable amount of the flavin mononucleotide is accumulated in the aqueous medium; and (2) recovering the flavin mononucleotide thus formed from the aqueous medium.

3. A recombinant DNA comprising a vector DNA and a DNA fragment which contains a gene coding for protein X, which is derived from *Escherichia coli*, has flavokinase activity and flavin adenine dinucleotide synthetase activity and has an amino acid sequence illustrated by SEQ ID NO:12, or a gene coding for the amino acid sequence of a modified protein X which has flavokinase activity and the amino acid sequence of protein X except that glycine at the residue number 23 is substituted with an amino acid selected from the group consisting of alanine, arginine and aspartic acid.

4. A microorganism which belongs to the genus Escherichia which harbors a recombinant DNA containing a DNA fragment which contains a gene coding for protein X, which is derived from *Escherichia coli*, has flavokinase activity and flavin adenine dinucleotide synthetase activity and has an amino acid sequence illustrated by SEQ ID NO:12, or a gene coding for the amino acid sequence of a modified protein X which has flavokinase activity and the amino acid sequence of protein X except that glycine at the residue number 23 is substituted with an amino acid selected from the group consisting of alanine, arginine and aspartic acid.

* * * * *